United States Patent [19]
Choate et al.

[11] Patent Number: 6,161,940
[45] Date of Patent: Dec. 19, 2000

[54] LARGE AREA COLLIMATED SUBSTAGE ILLUMINATORS FOR GAGING APPLICATIONS

[75] Inventors: Albert G. Choate, Rush; Edward Stokes, Rochester, both of N.Y.

[73] Assignee: Optical Gaging Products, Inc., Rochester, N.Y.

[21] Appl. No.: 09/186,392

[22] Filed: Nov. 5, 1998

[51] Int. Cl.[7] .................................................. F21V 1/00
[52] U.S. Cl. ........................ 362/235; 362/240; 362/244; 362/249; 362/351; 362/355
[58] Field of Search .................................. 362/235, 240, 362/244, 249, 351, 355, 367, 800, 97

[56] References Cited

U.S. PATENT DOCUMENTS

| | | | |
|---|---|---|---|
| 5,750,974 | 5/1998 | Sasaki et al. | 235/454 |
| 5,808,800 | 9/1998 | Handschy et al. | 359/630 |
| 5,897,195 | 4/1999 | Choate | 362/33 |

*Primary Examiner*—Sandra O'Shea
*Assistant Examiner*—John Anthony Ward
*Attorney, Agent, or Firm*—Shlesinger, Fitzsimmons & Shlesinger

[57] ABSTRACT

The illuminator includes a housing having thereon a transparent work supporting stage overlying an opening formed in the top of the housing. A plurality of light sources in the housing emit an array of spaced, parallel light beams through a like plurality of collimating lenses which collimate each of the beams emitted by the sources. The collimated light beams pass through a light transmissive diffuser which is interposed in the housing between its opening and the collimating lenses, which homogenizes the collimated light beams produced by said lenses. The homogenized light then passes through the housing opening, either directly or via one or more reflective surfaces, onto a workpiece located on the stage. In certain embodiments the collimated light beams pass through a beamsplitter before passage through the diffuser.

20 Claims, 4 Drawing Sheets

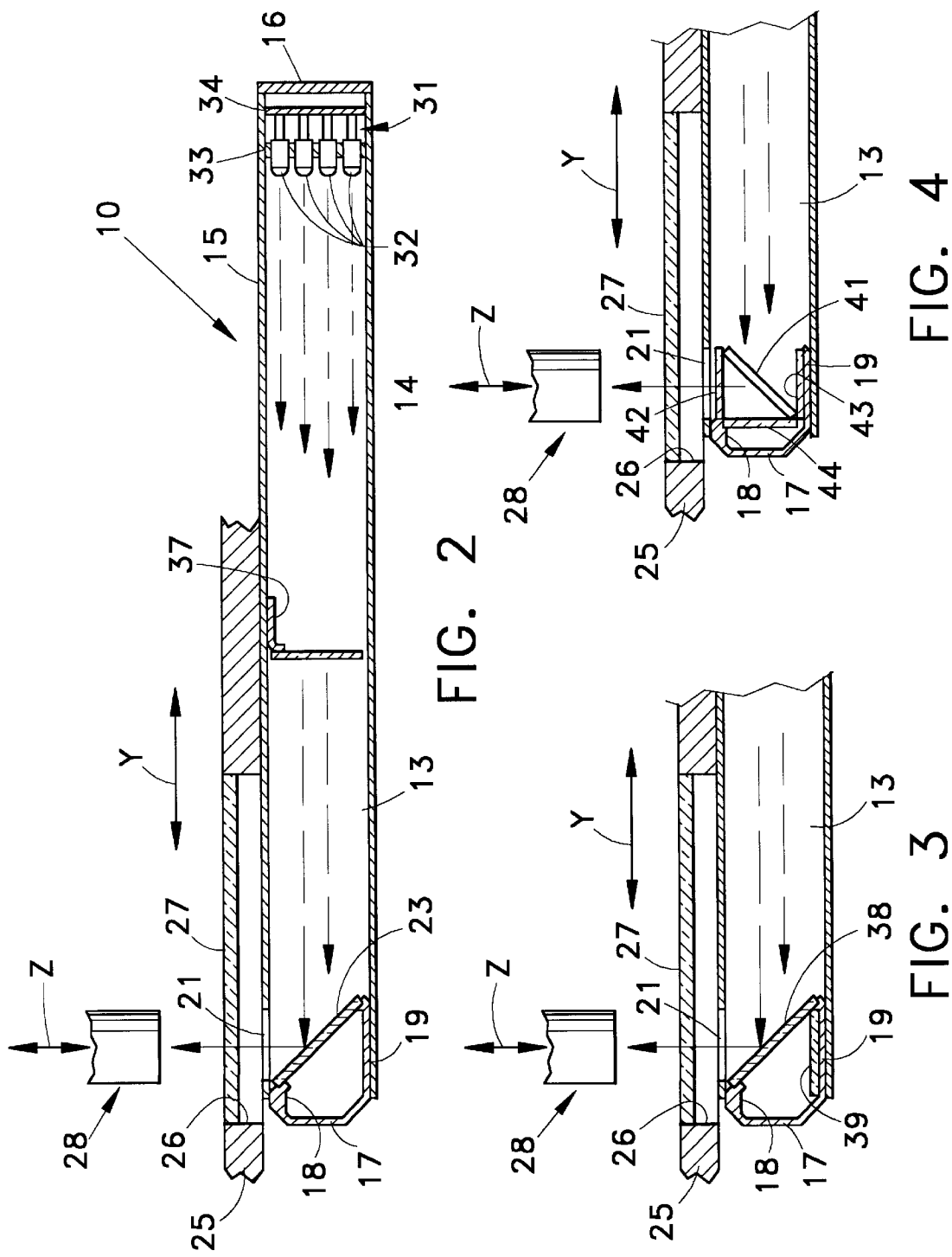

LARGE AREA COLLIMATED SUBSTAGE ILLUMINATORS FOR GAGING APPLICATIONS

BACKGROUND OF THE INVENTION

This invention relates to apparatus for inspecting manufactured parts or workpieces, and more particularly to an improved substage illuminator for producing acurate profiles or silhouettes of such parts for gaging or measuring purposes.

When using optical techniques to measure manufactured objects, whether employing visual or automated video methods, a magnification system is used to produce an enlarged image for evaluation. However, the means by which the object is illuminated can have very serious effects on the reliability of such measurements. For example, it is quite commonplace to utilize some form of substage illumination to produce a profile or silhouette of an object that is to be evaluated. If the object is examined on a typical diffuse-illumination light table which utilizes an array of fluorescent lights below a diffusive white glass, the image of the true edges of an inspected object are often confounded by scattered illumination. For example, when examining a cylindrical or spherical object, distorted images of the illuminated surfaces are reflected off the sides of the object, thus producing erroneous results.

To control this undesirable scattering of light, the so-called wall-effect problem, it has become customary to employ substage illumination which is collimated at least to some degree. In other words, the substage illuminator should provide illumination with sufficient angular range to fill the entrance pupil of the imaging optics, and be uniform over the measurement field. Also in some cases it may be necessary to move the optical system relative to the light table in order to inspect a large measurement area of the work or part that is being examined, so that properly maintaining registration of the substage light source with the imaging optics can be problematical.

It is an object of this invention, therefore, to provide an improved, colliimated substage illuminator, which is capable of illuminating a very large area, and which substantially eliminates the wall effect problem which was present in prior such illuminators. Still another object of this invention is to provide an illuminator of the type described which is capable of covering a very large area with collimated light beams capable of producing uniform illumination over a large measurement field.

Another object of this invention is to provide a substage illuminator having a large array of collimated light sources positioned beneath a light table and operative to direct collimated light beams through an adjacent beamsplitter or filter which eliminates dark zones between adjacent light sources.

Still another object of this invention is to provide an improved illuminator that does not have to be adjusted or repositioned, even though the imaging optics may have to be moved in order to inspect a very large area.

Other objects of the invention will be apparent hereinafter from the specification and from the recital of the appended claims, particularly when read in conjunction with the accompanying drawings.

SUMMARY OF THE INVENTION

The illuminator includes a housing having mounted thereon a transparent work supporting stage which is movable into different positions over an elongate opening formed in the upper wall of the housing, and beneath an optical system which overlies the stage. A plurality of light sources are mounted in the housing to direct an array of spaced, parallel light beams through a registering array of collimating lenses, and then through a homogenizing filter and the opening in the upper housing wall onto a workpiece supported on said stage. In certain embodiments the collimated light beams pass through the filter and then are reflected through the opening in the upper wall onto a workpiece, and in other embodiments the collimated light beams are reflected through the filter and opening onto a workpiece. Also, in certain embodiments the reflecting means includes a beamsplitter which can be employed with two mirrors to produce a double image of the array of collimated light beams.

THE DRAWINGS

FIG. 2 is a slightly enlarged sectional view of the illuminator taken along the line 2—2 in FIG. 1 looking in the direction of the arrows;

FIG. 3 is a fragmentary sectional view of a modified form of the means for producing illumination from the array of collimated light beams in the illuminator shown in FIG. 1;

FIG. 4A is a diagramatic illustration of the double image of the collimated light beams which are produced by the modified means shown in FIG. 4;

FIG. 5A is a diagramatic illustration of the array of light beams that are produced by the modified beamsplitters as shown in FIG. 5;

DETAILED DESCRIPTION OF THE PREFERRED EMBODIMENTS

Figure 1:
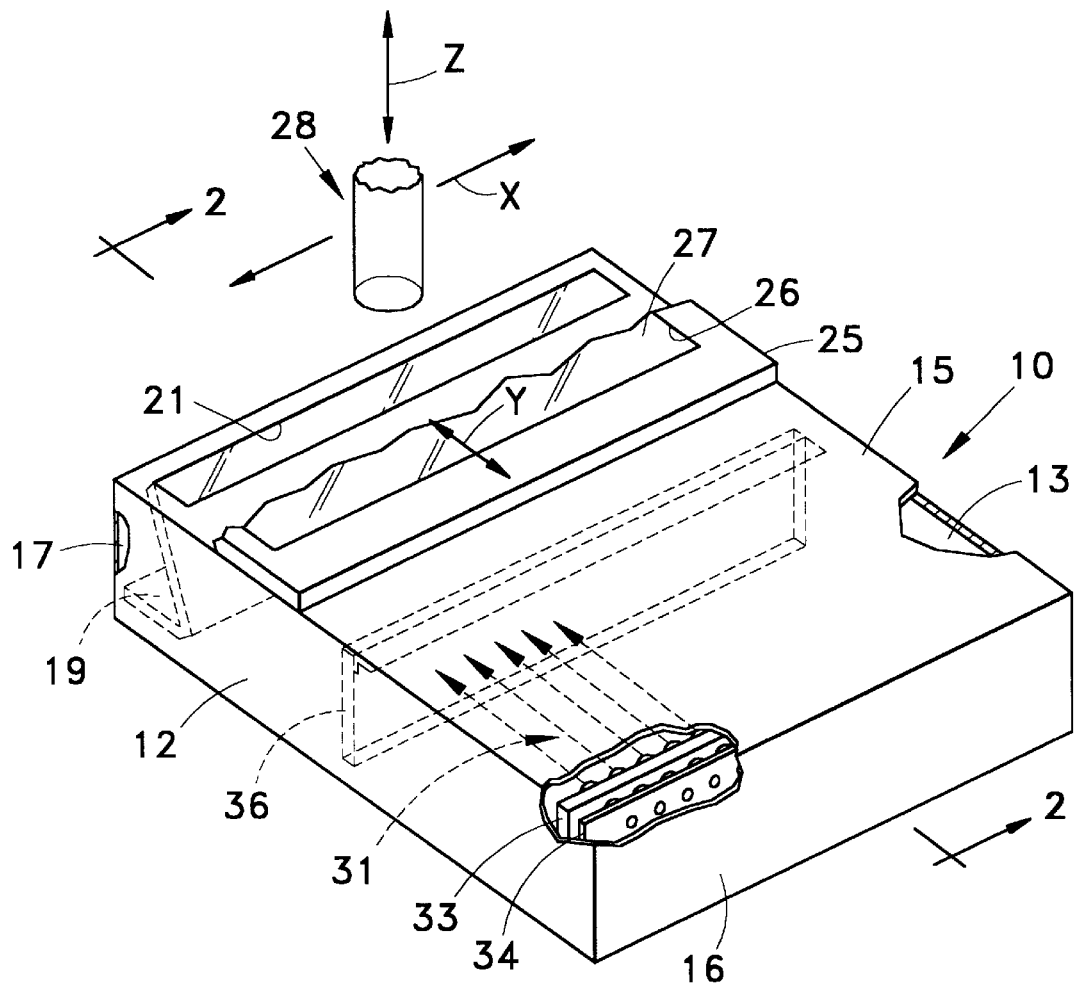
FIG. 1 is a fragmentary perspective view of a substage illuminator and associated optical system made according to one embodiment of this invention, the illuminator including improved means for producing a substage array of collimated light beams for producing a profile or silhouette of an object placed on the illuminator for inspection.

Referring now to the drawings by numerals of reference, and first to FIGS. 1 and 2, 10 denotes generally a substage illuminator housing having spaced, parallel side walls 12 and 13, a plane bottom wall 14 and a plane top wall 15 extending parallel to the bottom wall 14. The rear of the housing 10 is closed by an end wall 16 which extends transversely between the sidewalls 14 and 15. Housing 10 is closed at its forward end by another wall 17 that extends transversely between sidewalls 12 and 13, and which has adjacent its upper end a rearwardly extending flange section 18, which extends beneath and is secured to the forward end of the upper wall 15. At its lower end wall 17 has a rearwardly extending, planar flange section 19 which overlies and is secured to the upper surface of the bottom wall 14 adjacent its forward end.

For a purpose noted hereinafter, the upper housing wall 15 has therethrough adjacent its forward end an elongate, rectangularly shaped opening 21, which extends almost the full width of the upper wall 15 with the longitudinal side edges thereof extending parallel to the length of the front wall 17, and with opposite ends thereof being disposed in closely spaced, parallel relation to the opposed sidewalls 12 and 13. Mounted in the housing 10 beneath the slot or opening 21 to register therewith is an elongate, planar shaped mirror 23, which extends transversely between the housing sidewalls 12 and 13 in a plane inclined at approximately forty-five degrees to walls 14 and 15. Mirror 23 is secured adjacent its upper edge to the flange 18 of the front wall 17, and is secured at its lower edge to the inner end of flange 19, and in such manner that its upper, reflective surface is positioned beneath and in registry with opening 21. In practice, mirror 23 is at least equal in length to the opening 21.

Slidably mounted upon the upper housing wall 15 for adjustment in opposite directions transversely of the rear and front housing walls 16 and 17, or in the direction indicated by the arrows Y in FIGS. 1 and 2, is an upper stage or work support 25 having therein a large rectangular opening 26. Secured in the opening 26 is a large, rectangularly shaped plate 27 of glass or transparent material which is designed to have positioned thereon the workpiece or article that is to be examined by an associated optical system. In FIGS. 1 and 2, the optics head of this system is denoted generally by the numeral 28, and in practice is mounted to overly the slot or opening 21 for adjustment longitudinally thereof or in the X direction as shown in FIG. 1, as well as being adjustable vertically in the direction denoted by the letter Z in FIGS. 1 and 2. In practice, therefore, the workpiece mounted on the plate 27 can be adjusted in the Y direction by the stage 25 in order to shift different portions of the workpiece over the slot 21 and beneath the optics head 28, for inspection thereby. Likewise, of course, the head 28 may be shifted longitudinally of the slot 21, and hence in the direction X relative to any portion of the workpiece that overlies slot 21.

Secured in housing 10 adjacent its rear wall 16 is a light source array, which is denoted generally by the numeral 31. In this first embodiment the light source array 31 comprises a plurality of light emitting diodes (LEDs) 32 which are secured intermediate their ends in registering, circular openings formed in a rectangular panel 33, which is secured in housing 10 in spaced, parallel relation to its rear wall 16. The LEDs 32 are mounted in panel 33 in such manner that the light emitting ends thereof, which in this first embodiment have collimating lenses molded thereover, all face in the direction of the mirror 23, and are arrayed in spaced, parallel rows that extend transversely between the opposed sidewalls 12 and 13 of the housing, and in spaced, parallel, vertical columns that extend transversely between the walls 14 and 15 of the housing. To supply the necessary power for the LEDs 32, the ends remote from their light emitting ends are connected to a printed circuit panel 34, which is secured in housing 10 in the space between its backwall 16 and the LED supporting panel 33.

As a result of this construction, and as illustrated by the arrows and broken lines in FIGS. 1 and 2, the collimated light beams from the LEDs 32 pass through a diffuser 36, which extends transversely across the center of the housing 10 between its sidewall 12 and 13, after which the diffused light falls on the face of mirror 23 and is directed vertically thereby through the housing opening 21 and the transparent plate 27 onto a work or part (not illustrated) that is placed thereon to be inspected. The diffuser 36, which may be secured adjacent its upper edge to the underside of the housing topwall 15 by a bracket 37, functions as a beam homogenizer, which eliminates hot spots or variations in brightness which typically is caused by the closely spaced LEDs 32. Diffusers of this type are offered for sale by Physical Optics Corporation; and the LEDs 32 of the type noted above are offered for sale by Hewlett Packard under the designation HLMA-CHOO/-CLOO. Diffuser 36 functions to cause the individual, collimated beams of light from array 31 to blend together thereby effecting a more spatially and angularly uniform distribution of the illumination.

Referring now to the embodiment shown in FIG. 3, wherein like numerals are employed to denote elements similar to those employed in the first embodiment (FIGS. 1 and 2), the apparatus is similar to that of the first embodiment, except that the mirror 23 is replaced by a beamsplitter 38, Also an elongate, rectangularly shaped retro-reflector 39 of planar configuration is secured to the upper surface of flange section 19 of the housing wall 17 so that its plane upper surface is disposed at an angle of approximately forty five degrees with the beamsplitter 38. This construction is particularly suitable when the imaging optical system includes means for directing illumination downwardly onto the upper surface of an object that is placed upon the transparent table 27 for inspection purposes. Certain of this downwardly projected illumination passes through the plate 27 and can be reversed by the upper surface of the retro-reflective material 39, thus producing an effect which is similar to substage illumination. Alternatively, the reflective material 39 may comprise a simple mirror.

Figure 4:
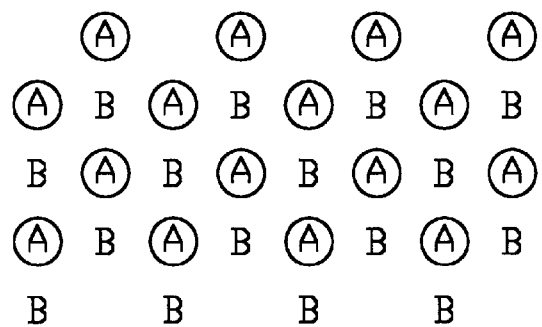
FIG. 4 is a fragmentary sectional view of another modified means of producing the array of collimated light beams in the illuminator of FIG. 1, and which means includes a beamsplitter for producing a double image of the light beams.

Referring now to the embodiment shown in FIG. 4, wherein like numerals are employed to denote elements similar to those employed in the preceding embodiments, the mirror 23 of the first embodiment is replaced by a beamsplitter 41 which registers with the opening 21 in the housing, and is inclined in a plane which extends at approximately forty-five degrees to the walls 14 and 15, but in a plane that is inclined at 180° to the plane containing the mirror 23 in the first embodiment. Also, unlike the first embodiment, a diffuser 36 is not located centrally in the housing 10 between the mirror 23 and the array 31 of the light sources. Instead, in the embodiment shown in FIG. 4, a diffuser 42 is mounted above the beamsplitter 41 and lies in a plane parallel to and is disposed beneath the plane containing the opening 21. Also, a plane, flat mirror 43 is secured on the upper surface of the flange 19 on the front housing wall 17, and another mirror 44 is secured to and extends transversely between flanges 18 and 19 of the wall 17 to have its surface disposed in a plane extending at apprxoimately forty-five degrees to the surface of the beamsplitter 41 that faces the opening 21. The effect of using the beamsplitter 41 in combination with the two reflectors or mirrors 43, 44 is to form two images of the collimated light beams produced by the LED array 31. FIG. 4A illustrates diagramatically the two images of the beams that are produced by the two mirrors, the beams reflected by mirror 41, for example, being denoted by the letters A, while the beams reflected by mirror 44 are denoted by the letters B. While this increases the density of the reflected, collimated beams, nevertheless there is a need for providing more uniform distribution of the beams, and this is effected by use of the diffuser 42, which functions in a manner similar to diffuser 36 in the first embodiment to provide more uniform distribution of the illumination.

Figure 5:
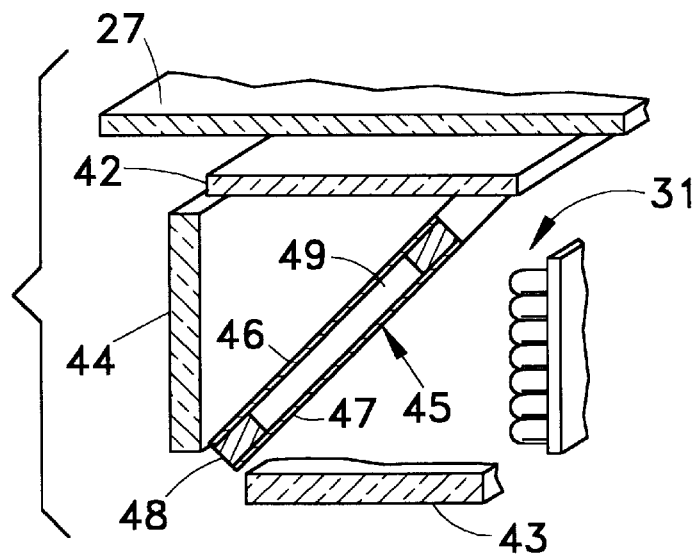
FIG. 5 is a slightly enlarged fragmentary sectional view of the means for producing collimated light beams similar to that shown in FIG. 4, but employing a modified beamsplitter for producing multiple images of the light beams.
Figure 5:
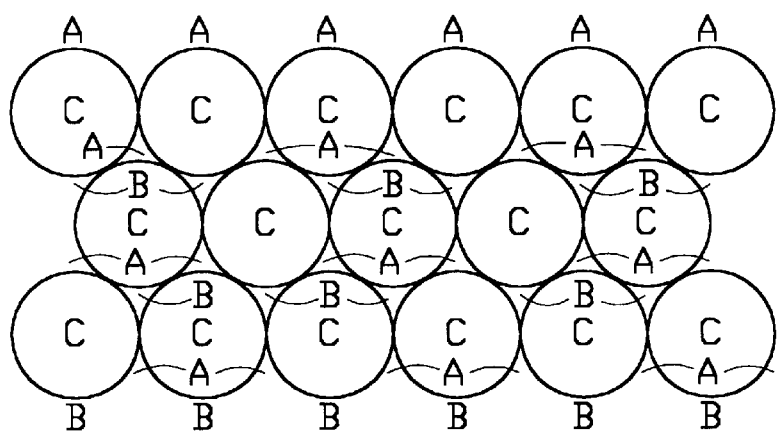

FIG. 5 illustrates a modified form of the substage illuminator shown in FIG. 4, and for that reason parts similar to those shown in FIG. 4 are shown schematically. The only difference between the embodiment shown in FIG. 5 and that shown in FIG. 4 is that a special beamsplitter is employed in this embodiment. The modified beamsplitter, which is denoted generally by the numeral 45, comprises two separated layers 46 and 47 of thin, light transmissive materials, such as thin glass or plastic films having natural reflective properties. The layers 46 and 47 are secured to opposite sides of a rectangularly shaped frame 48 having therethrough a central, rectangularly shaped opening 49 opposite ends of which are covered by the layers 46 and 47. These layers in effect provide two, separated, parallel beamsplitter surfaces, each layer having roughly 4% reflection on each surface thereof, or 8% per layer. In practice they can be spaced approximately 2 mm apart.

The result of the construction shown in FIG. 5 is that the collimated light beams produced by the array 31 produce three superimposed images of light beams upon passing through the beamsplitter 45. The resultant three superimposed images are illustrated, for example, in FIG. 5A, and are represented by the letters A, B and C. As previously noted, the diffuser 42 functions to homogenize the numerous beams, thus providing a more uniform distribution of the illumination directed toward the transparent stage 27.

Figure 6:
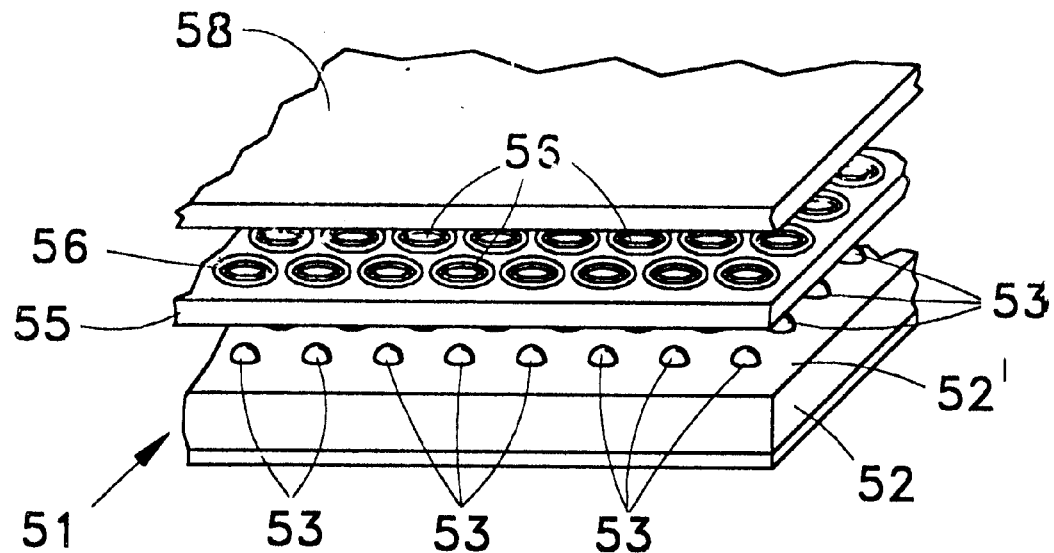
FIG. 6 is a fragmentary sectional view of still another mean of producing an array of collimated light beams which may be employed in the illuminator shown in FIG. 1.

In the foregoing embodiments the LEDs have been defined as being the type having plastic collimating lenses molded over the light emitting ends thereof, so that the LEDs produce collimated light beams. However, it is anticipated that substage illuminators of the type described can use other forms of light sources, such as for example light sources in the form of incandescent lamps, fiber optics or LEDs which do not have collimating lenses molded or otherwise secured over the light emitting ends thereof. FIG. 6, for example, illustrates fragmentarily an array of light sources which is denoted generally by the numeral 51. Array 51 comprises a planar dielectric or plastic substrate 52 having secured therein in spaced, parallel rows and intersecting, parallel columns a plurality of light sources, for example simple LEDs, incandescent lamps or fiber optic light sources each of which is denoted by the numeral 53. The light emitting ends of the lamps 53 register with or extend slightly above the surface 52' of the substrate 52, which in FIG. 6 is the upper surface of substrate 52.

Mounted in spaced, parallel relation to the substrate 52 is a planar panel or sheet 55 having formed therein a plurality of Fresnel lenses 56, which are arranged in spaced, parallel rows and intersecting columns, so that each of the lenses registers with the light emitting end of one of the light sources 53 in the substrate 52. Mounted in spaced, parallel relation to the panel 55 at the side thereof remote from the substrate 52 is a planar diffuser 58, which may be of the type noted above that is offered for sale by Physical Optics Corporation. As a result of this construction, the light beams emitted by the light sources 53 are collimated as they pass through the registering Fresnel lenses 56, and the array of collimated light beams directed by the Fresnel lenses toward the diffuser 58 are homogenized by the diffuser 58 before being transmitted thereby to a transparent work support, such as for example the transparent table or upper stage denoted by the numeral 27 in the first embodiment. The advantage of the construction as shown in FIG. 6, is that, if desired, the array 51 of the light sources and the associated lenses 57 and overlying diffuser 58 could be positioned directly beneath the slot 21 in a housing of the type denoted by numeral 10, in which case it would be possible to eliminate the light source array 31 and diffuser 36 shown in FIG. 1.

Figure 7:
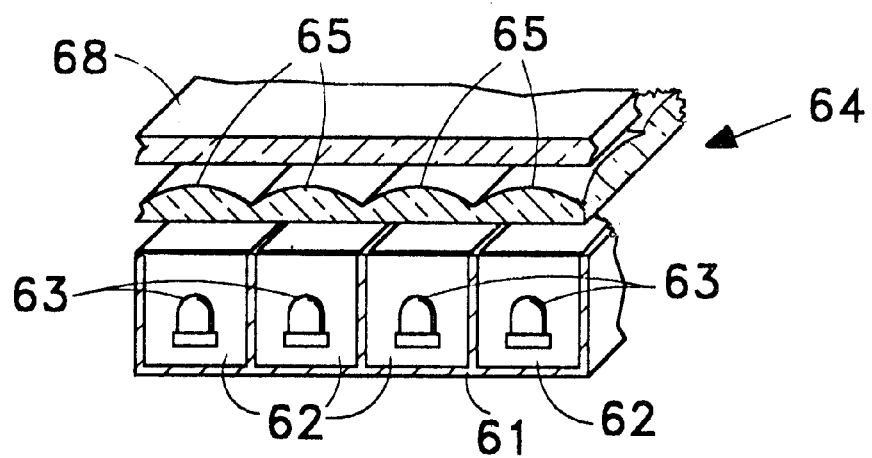
FIG. 7 is a fragmentary sectional view of still another means of producing the collimated light beams in the illuminator of FIG. 1.

As a further alternative for supplying collimated light beams for a substage illuminator, FIG. 7 shows a panel or substrate 61 having therein a plurality of spaced openings 62 which are arranged in parallel rows and intersecting, parallel columns in the substrate 61. Moreover each recess 62 has mounted therein a light source 63, the light emitting end of which, when the light source is energized, directs a beam of light onto the underside of a lenticular array 64 of collimating lenses 65. Overlying the array 64 of lenses 65 is, once again, a diffuser or equalization filter 68 which performs the same function as the filter 58 referred to in FIG. 6. As in the case of the embodiment shown in FIG. 6, the light sources 63 contained in the substrate 61 may consist of incandescent lamps, fiber optics or simple LEDs which do not have collimating lenses molded or otherwise secured over the light emitting ends thereof. Instead, this function is performed by the lenticular array 64 of collimating lenses. And, as in the case of the embodiment shown in FIG. 6, the embodiment shown in FIG. 7 can be utilzed in an illuminator housing, such as housing 10, so as to be secured in the housing beneath and at registry with the slot 21, thereby replacing the light source array 31 and the diffuser 36.

From the foregoing it will be apparent that the present invention relates to the production of a large area of substage illuminator that does not have to be repositioned in order to maintain its alignment with the transparent, work-supporting stage. While the invention has been illustrated and described in detail in connection with various embodiments thereof, it will be apparent that the invention is suitable for use with illuminator housings in which the opening 21 and associated array of light sources differ in shape and in size from that illustrated herein. Moreover, it will be apparent that it is not necessary that each of the light sources in a given array thereof be simultaneously illuminated or energized each time it is desired to inspect a workpiece on the transparent stage 27. Obviously the light sources can be selectively energized to direct illumination only to that area of the opening 21 which is positioned beneath or adjacent to a part that is to be inspected on the stage 27. Also, while this invention has been illustrated and described in detail in connection with only certain embodiments thereof, it will be apparent that it is capable of still further modification, and that this application is intended to cover any such modifications that fall within the scope of one skilled in the art or the appended claims.

What is claimed is:

1. In gaging apparatus for examining a workpiece positioned beneath an optics head for inspection thereby, an improved substage profile illuminator comprising a housing positioned beneath said optics head and having therein a chamber, a transparent work supporting stage mounted on said housing over an opening formed in said housing adjacent one end of said chamber to register with said optics head, said stage disposed to have a workpiece positioned thereon at the exterior of said chamber, a plurality of light sources mounted in said chamber in spaced, parallel rows with the light emitting ends in each row thereof positioned to direct in a common plane and in the same direction an array of spaced, parallel light beams from those of the light sources that are energized, and means operative to direct illumination from said array of beams through said opening and onto the underside of a workpiece positioned on said stage to produce a silhouette of the workpiece for observation by said optics head, said means including a plurality of collimating lenses interposed between said opening and the light emitting ends of said light sources and operative to collimate each of the beams emitted by said energized sources, and said means further including a light transmissive diffuser interposed between said opening and said collimating lenses and operative to homogenize the collimated light beams produced by said lenses.

2. A substage profile illuminator as defined in claim 1, wherein the area of said array of light beams produced by energization of all of said light sources approximately equals the area of said opening in said housing, whereby said entire opening is illuminated by said homogenized light beams.

3. A substage profile illuminator as defined in claim 1, wherein said work supporting stage is mounted for limited movement on said housing relative to said opening.

4. A substage profile illuminator as defined in claim 1, wherein each of said light sources comprises a light emitting diode having one of said collimating lenses secured over the light emitting end thereof.

5. A substage profile illuminator as defined in claim 4, wherein said diffuser is positioned in a plane extending transversely of said collimated light beams, the light emitting ends of said diodes are arrayed in a plane extending parallel to and spaced from the plane containing said diffuser, and said means further includes reflector means positioned between and registering with said opening and said diffuser and operative to reflect into said opening the homogenized light produced by said diffuser from said collimated light beams.

6. A substage profile illuminator as defined in claim 5, wherein said reflector means comprises a mirror mounted in said chamber with the reflective surface thereof registering with said opening and the homogenized light beams from said diffuser, and disposed in a plane, inclined to the plane containing said diffuser.

7. A substage profile illuminator as defined in claim 5, wherein said reflector means comprises a beam splitter mounted in said chamber with one side thereof disposed in registry with said opening and extending transversely of the homogenized light beams from said diffuser, and a reflective surface mounted in said chamber at the opposite side of said beamsplitter and disposed to reflect light from said beamsplitter to said opening.

8. A substage profile illuminator as defined in claim 4, wherein said diffuser is mounted in said chamber to extend in a plane parallel to and to cover the inner end of said opening, and said means further includes reflector means mounted in said chamber between said diffuser and said collimating lenses and operative to reflect collimated beams from said lenses through said diffuser and said opening to a workpiece positioned on said stage.

9. A substage profile illuminator as defined in claim 8, wherein said reflector means comprising a first mirror mounted in said chamber beneath and in spaced, parallel, confronting relation to said diffuser, a beamsplitter mounted in said chamber in the space between said diffuser and said first mirror and having opposite sides thereof lying in spaced, parallel planes inclined diagonally between said diffuser and said first mirror, one side of said beamsplitter facing and extending transversely of said collimated light beams, and the other side of said beamsplitter confronting upon a second mirror that extends at right angles between said diffuser and said first mirror.

10. A substage profile illuminator as defined in claim 9, wherein said beam splitter comprises a rectangularly shaped frame having therethrough a central, rectangular opening, and a pair of spaced, parallel thin layers of light transmissive material secured over opposite sides, respectively, of said frame and said opening therein, each of said layers having natural reflective properties.

11. A substage profile illuminator as defined in claim 1, wherein said diffuser is mounted in said cHamber to extend in a plane parallel to and to cover the inner end of said opening, said light sources are mounted in said chamber beneath said diffuser and with said light emitting ends thereof facing said diffuser and lying in a plane parallel thereto, and said collimating lenses are mounted in a common plane positioned between and in spaced, parallel relation to said diffuser and the plane containing said light emitting ends of said light sources.

12. A substage profile illuminator as defined in claim 11, wherein said collimating lenses comprise a plurality of Fresnel lenses mounted in said common plane.

13. A substage profile illuminator as defined in claim 11, wherein said collimating lenses comprises a lenticular array thereof disposed in said common plane.

14. In combination with a transparent work supporitng stage disposed to have a workpiece supported thereon, and an optical system having an adjustable lens mechanism overlying said stage for observing a workpiece mounted thereon, a substage illuminator positioned beneath said stage and comprising a housing having an upper wall thereof extending beneath said stage, and having therein an opening registering with said stage and said optical system, a plurality of light sources mounted in said housing beneath said upper wall in spaced parallel rows with the light emitting ends in each row thereof lying in a common plane, and selectively operable to emit in a common plane and in the same direction an array of spaced, parallel light beams, means in said housing for directing illumination from said array of beams upwardly through said opening in said upper wall and onto the underside of a workpiece positioned on said stage to produce a silhouette of the workpiece for observation by said optical system, said means including a plurality of collimating lenses interposed between said opening and the light emitting ends of said light sources and operative to collimate each of the beams emitted by said sources, and said means for further including a light transmissive diffuser interposed between said opening and said collimating lenses and operating to homogenize the collimated light beams produced by said lenses.

15. In the combination as defined in claim 14, wherein the area of the collimated light beams produced by operation of all of said light sources is equal to or greater than the area of said opening in said upper wall of said housing.

16. In the combination as defined in claim 15, wherein said opening in said upper wall of said housing is positioned adjacent one end of said housing, said light sources are mounted in said housing adjacent the opposite end thereof with said light emitting ends thereof facing said one end of said housing and arrayed in spaced, parallel rows, and spaced, parallel intersecting columns in said common plane, and said means further includes reflective means mounted in said housing in registry with said opening and said diffuser, and operative to reflect the homogenized light beams from said diffuser through said opening to a workpiece positioned on said stage.

17. The combination as defined in claim 16, wherein each of said light sources comprises a light emitting diode having one of said collimating lenses secured over the light emitting end thereof.

18. The combination as defined in claim 16, wherein said diffuser is mounted in said housing to extend in a plane disposed in spaced, parallel relation to the plane containing the light emitting ends of said light sources, and in spaced, confronting relation to said reflective means.

19. The combination as defined in claim 16, wherein said reflective means includes a beam splitter mounted in said housing with one surface thereof disposed in a plane inclined to and registering with both said opening and said diffuser.

20. The combination as defined in claim 14, wherein said diffuser is mounted in said housing beneath said upper wall thereof to extend in a plane parallel to and to cover the inner end of said opening, said light sources are mounted in said housing beneath said diffuser and with said light emitting ends thereof facing said diffuser and lying in a plane parallel thereto, and said collimating lenses are mounted in a common plane positioned between and in spaced, parallel relation to said diffuser and the plane containing said light emitting ends of said light sources.

* * * * *